United States Patent [19]
Martin et al.

[11] Patent Number: 5,057,419
[45] Date of Patent: Oct. 15, 1991

[54] GENETICALLY ENGINEERED PLASMID AND ORGANISMS FOR THE PRODUCTION OF SPECIALIZED OILS

[75] Inventors: Charles E. Martin, Somerset; Robert M. Johnston, Middletown, both of N.J.

[73] Assignee: Rutgers University, New Brunswick, N.J.

[21] Appl. No.: 247,918

[22] Filed: Sep. 22, 1988

[51] Int. Cl.$^5$ .............................................. C12P 7/64
[52] U.S. Cl. .................................. 435/134; 435/255; 435/320.1; 536/27
[58] Field of Search ...................... 435/41, 69.1, 69.9, 435/71.1, 134, 172.3, 189, 224, 240.4, 240.5, 240.51, 252.3, 255, 256; 935/33, 35, 37, 42, 67, 69

[56] References Cited

U.S. PATENT DOCUMENTS 4,661,454  4/1987  Botstein et al. ..................... 935/22
4,771,002  9/1988  Gelvin et al. ...................... 435/253

OTHER PUBLICATIONS

Thiede et al., The Journal of Biological Chemistry, vol. 261, No. 28, Oct. 5, pp. 13230-13235 *Stearyl Coenzyme Adesatinase*.
"The OLE 1 Gene of *Saccharomyces cerevisiae* Encodes the Δ9 Fatty Acid Desaturase and Can Be Functionally Replaced by the Rat Stearoyl-CoA Desaturase Gene," Stukey, J. E. et al., *J. Biol. chem.* 265:20144-149 (1990).
"Nile Red: A Selective Fluoroscent Stain for Intracellular Lipid Droplets", Greenspan, P. et al., *J. Cell Biol.* 100:965-973 (1985).
"Spectrofluorometric Studies of the Lipid Probe Nile Red", Greenspan, P. and S. D. Fowler, *J. Lipid Research* 26:781-789 (1985).
"Enzyme Nomenclature", Commission on Biochemical Nomenclature, Academic Press, pp. 127, 550 (1979).
"Biological Research on Industrial Yeast Vol. I", Stewart, G. G. et al., eds., CRC Press, p. 2 (1987).
"Microbiology", A. I. Braude ed. W. b. Saunders Co., pp. 134-35 (1982).
"Bacterial Synthesis of Active Rat Stearl-CoA Desaturase Lacking the 26-Residue Amino-Terminal Amino Acid Sequence", Strittmatter, P. et al., *J. Biol. Chem.*, 263:(5):2532-35 (1988).
"Isolation and Characterization of OLCl, a Gene Affecting Fatty Acid Desaturation from *Saccharomyces cerevisiase* Stuckey", J. E. et al., *J. Biol. Chem.*, 264(28):16537-16544 (1989).
"Nutritional Regulation of Yeast -9 Fatty Acid Desaturase Activity", Bossie, M. and C. E. Martin, *J. Bacteriol.* 171(12): 6409-6413 (1989).

*Primary Examiner*—Richard A. Schwartz
*Attorney, Agent, or Firm*—H. Hunter Jervis

[57] ABSTRACT

A DNA fragment containing a gene encoding a fatty acid desaturase enzyme is isolated. The gene is then employed by introducing it into other cells to alter or enhance the production of oils in such cells, alternatively the gene or nucleic acid sequences of the gene can be employed to isolate other genes encoding for related, but different desaturase enzymes.

20 Claims, 1 Drawing Sheet

GENETICALLY ENGINEERED PLASMID AND ORGANISMS FOR THE PRODUCTION OF SPECIALIZED OILS

BACKGROUND OF THE INVENTION

This invention relates to the production of specialized oils by genetically engineered organisms and the plasmids, vectors and organisms related thereto.

DESCRIPTION OF REPORTED DEVELOPMENTS

Plasmids are autonomously replicating, normally cyclic, double-stranded DNA molecules which usually do not normally form part of the cellular chromosome and which are believed to carry genetic information which is not essential for the growth of the host cell, whilst the chromosome carries all of the essential genetic information. The plasmids are described as "normally cyclic" as this is the form that they may be seen to adopt in isolation under laboratory conditions; the form adopted under other conditions may or may not be different. The functions in nature of certain plasmids have been discovered, for example, some are known to code for apparatus (e.g. enzymes) providing the host cell with resistance to antibiotics, but many plasmids are "cryptic," i.e., their function in the cell has not been elucidated.

In the field of genetic engineering, however, plasmids are invaluable, in that they provide three different, but related, functions. First they provide a mechanism whereby a selected DNA molecule (generally coding for some valuable function, such as the production of proinsulin or interferon) may be multiplied many times by natural biological activity; this is called "cloning". Second, they provide a mechanism whereby the activity of that DNA molecule may be expressed, i.e., a cell may be induced to produce a material by incorporating the genetic information coding for the desired material on a plasmid in the form of an added DNA molecule and incorporating that plasmid into a living cell. Third, they act as transportation vectors to move DNA from one genome to another.

The insertion of a DNA molecule containing desired genetic information into a plasmid is effected by cleaving the plasmid and then splicing the length of added DNA molecule onto each of the free ends of the cleaved plasmid, to reform a larger cyclic DNA molecule, i.e., a larger plasmid. This cleavage is effected by means of an enzyme known as a restriction endonuclease, which catalyses the hydrolysis of the DNA molecule at one or more specific sites. The activity of a particular endonuclease is limited to the catalysis of hydrolysis at a characteristic site and thus causes cleavage of the plasmid at that site.

The role of vectors in gene engineering is stated clearly in Recombinant Molecules: Impact on Science and Society, Miles International Symposium Series No. 10, edited by R. F. Beers and E. G. Basset, Raven Press, N.Y. The usefulness of plasmids as vectors in gene engineering is recognized on the host-vector system of *Escherichia coli*. Recombinant DNA technology has also been developed in respect of industrially useful microorganisms other than *E. coli*, such as amylase-producing *Bacillus subtilis*, antibiotic producing Actinomycetes and alcohol producing yeasts such as *Saccharomyces cerevisiae*, methylotropic yeasts such as *Pichia pastoris*, dimorphic yeasts such as *Yarrowia lipolytica*, and Ascomycete fungi such as *Neurospora crassa* and *Aspergillus nidulans*. Since vectors are important in recombinant DNA technology, plasmids have been developed for use in these microorganisms. Plasmids have also been developed for use in the expression of genes in a variety of plant and animal systems.

In *Saccharomyces cerevisiae* plasmid vectors have been constructed which autonomously replicate in that organism in multiple copies per cell (plasmids containing sequences of the yeast 2 micron circle plasmid or autonomously replicating sequences derived from yeast chromosomes), as single copies per haploid cell (centromere containing plasmids) and as plasmid vectors that can be integrated into regions of yeast chromosomes (Integrating plasmids). These plasmid vectors have also been engineered so that they can be replicated in E. coli for purposes requiring amplification and analysis of plasmid DNA.

SUMMARY OF THE INVENTION

In accordance with the present invention, a DNA fragment containing a gene encoding a fatty acid desaturase enzyme was isolated. A plasmid expression vector which gives rise to an over expression of oil production has been constructed from the fragment which contains the fatty acid desaturase gene. Further, the plasmid expression vector was introduced into an organism and the resultant, recombinant strain of organism was cultured and uncharacteristically large quantities of oil were produced. Additionally, the DNA fragment encoding the desaturase gene and information derived from its DNA sequence can be employed to isolate genes encoding related enzymes from yeast and other organisms which can then be used in a similar manner to elicit increased production of oils with defined fatty acid compositions.

DETAILED DESCRIPTION OF THE INVENTION

Figure 1:
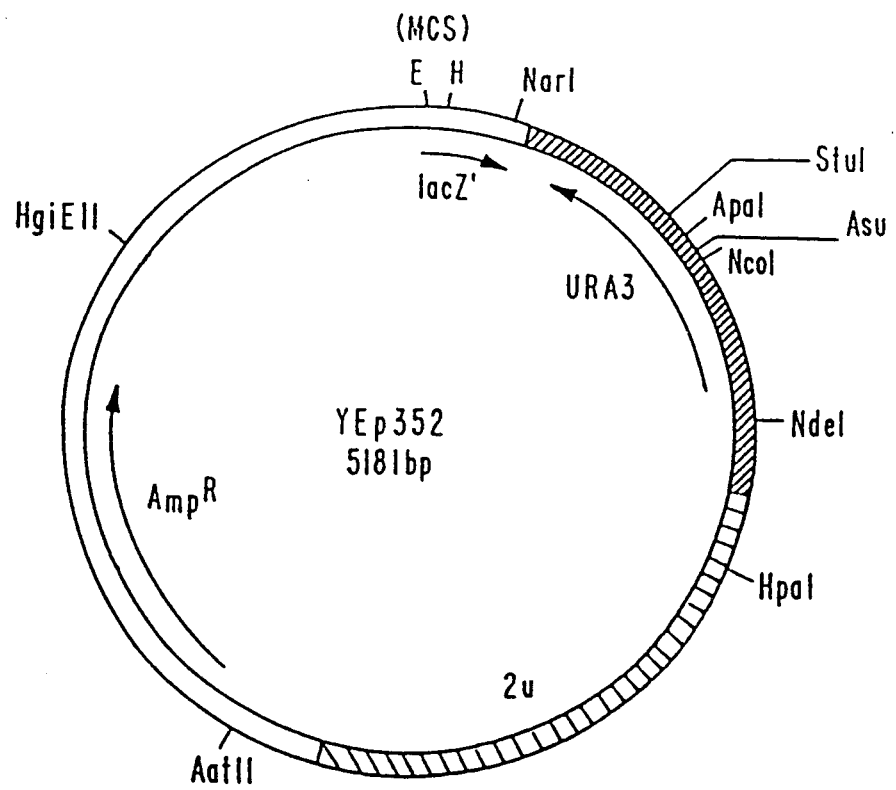
FIG. 1 illustrates the construction of vectors useful for production of desaturase enzymes in yeast as described in detail below.
Figure 1:
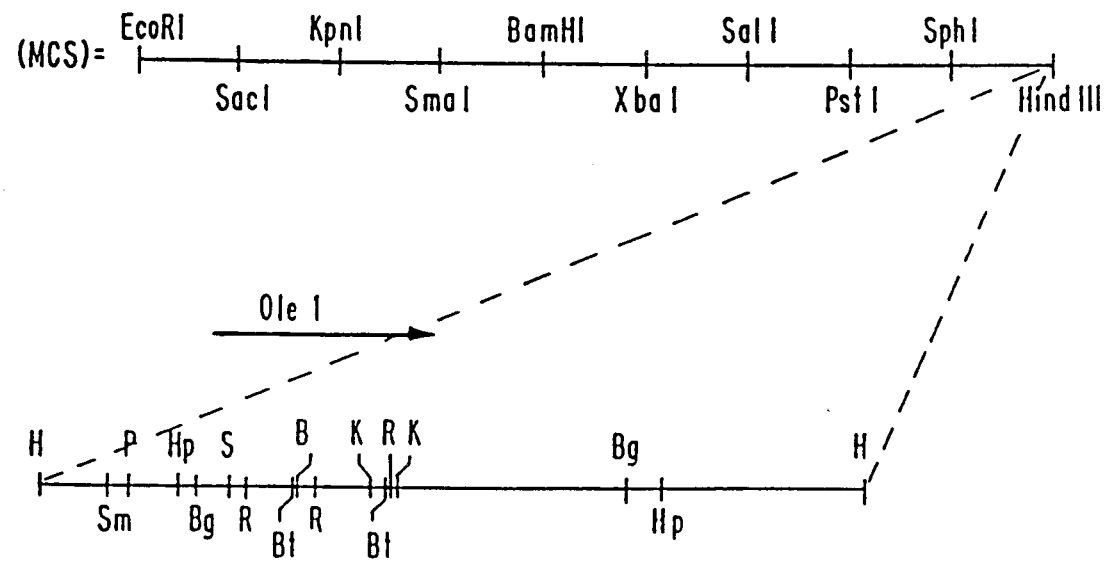

Generally, a DNA fragment containing a fatty acid modifying gene has been discovered that, when introduced into a organism, causes cells of that organism to produce an abundance of high purity oils with specific fatty acid compositions. A plasmid expression vector containing said gene, which functions in yeast and other organisms, is cloned in such a manner as to allow for the expression of the gene so that specialized oils useful for food, pharmaceutical and lubrication purposes are produced by the organism. In addition, the invention provides for the modification of a yeast strain or other organism by incorporating the above described expression plasmid, or similar plasmids which over express a fatty acid desaturase gene contained in that plasmid or plasmids which integrate into the DNA of a host organism and which strain, or organism, produces high levels of specialized oils. It should be understood that the DNA fragment referred to herein is a restriction fragment which may consist entirely of the desired gene or may comprise the gene along with other DNA sequences.

The process described herein is applicable to the production of high yield, high quality specialized oils that may be produced in organisms ranging from yeast to field crops. Some examples of applications of the invention also include producing high yields of triglycerides with high levels of oleic acid in yeast; causing yeast (or other organisms) to overproduce oils containing polyunsaturated fatty acids having superior lubricating, nutritional, cooking and temperature related properties by causing enhanced production of corresponding fatty acid desaturating enzymes in the organisms; and reducing the cost of brewing manufacture and specialty oil production concurrently by using engineered strains of yeast as described herein.

In a more specific aspect of the invention, a DNA fragment has been isolated from yeast that contains a gene that encodes for production of delta-9 fatty acid desaturase. The gene lies within a 4.8 kilobase HindIII restriction fragment of a *Saccharomyces cerevisiae* (bakers yeast) DNA library derived from a diploid laboratory strain R254 of that organism. Other laboratory strains are known to contain the gene in different sized HindIII fragments as shown in TABLE 1, however, for purposes of the ensuing discussion the DNA fragment containing the yeast delta-9 desaturase gene will be referred to as the 4.8 kb HindIII fragment.

TABLE 1

Approximate sizes of HindIII restriction fragments containing the delta-9 desaturase gene from different laboratory strains of *Saccharomyces cerevisiae*.

| Strain | Size (kb) |
| --- | --- |
| S288C | 5.7 |
| DBY 747 | 5.7 |
| DC6 | 4.8 |
| R254 (diploid) | 4.8 |
|  | 8.6 |

Introduction of a plasmid containing multiple copies of the desaturase gene or containing a single copy of the gene controlled by a strong promoter element, into *Saccharomyces cerevisiae* results in an organism with enhanced ability for the production of certain specialized oils.

Proof that the 4.8 kb HindIII restriction fragment includes the gene encoding the fatty acid desaturase is derived from DNA sequence analysis indicating that the encoded protein by that DNA fragment has significant amino acid homology with the protein encoded by the recently isolated cDNA clone of the rat liver enzyme, the two proteins having an overall identity of greater than 30% with several perfectly matching consecutive sequences. Furthermore, when genetic manipulations in which parts of the cloned DNA sequence are used to disrupt the gene in wild type cells the result is the production of a strain of yeast devoid of fatty acid desaturase activity, producing a strict requirement for unsaturated fatty acids for growth. The gene complements the unsaturated fatty acid requiring ole-1 mutant and two similar mutants isolated in our laboratory. The particular DNA sequence encoding the a portion of the yeast delta-9 fatty acid desaturase enzyme is given in Table 2 appearing at the end of the specification.

The oil production associated with the introduction of the gene appears to be the result of over expression of the gene beyond normal cellular levels resulting in increased fatty acid desaturase activity. This can occur by either the introduction of multiple copies of the functional desaturase gene into yeast by way of a multiple copy plasmid or by way of introduction of copies of the gene which can be over expressed by the construction of a plasmid containing the desaturase gene under the control of a strong promoter element such as, but not limited to the Gal1- or Gal10 promoters from *Saccharomyces cerevisiae*. An example of an engineered plasmid and a *Saccharomyces cerevisiae* strain constructed for maximal expression of a specific gene other than a fatty acid desaturase gene is given in Schultz, et al. "Regulated overproduction of the GAL4 gene product greatly increases expression from galactose-inducible promoters on multi-copy expression vectors in yeast.", Gene, Volume 61, (1987) pages 123–133 which is incorporated herein by reference.

Introduction of the enhanced fatty acid desaturase activity into either wild type, or unsaturated fatty acid requiring yeast mutants causes the production of large oil-like droplets in the cytoplasm of the cells as revealed by phase contrast microscopy. Staining the cells with the fluorescent stain, Nile Red, reveals that the droplets fluoresce intensely at wavelengths characteristic of a triglyceride environment.

While the invention is described herein in terms of enhancing oil production in *Saccharomyces cerevisiae*, it will be understood by those skilled in the art that enhancement can be effected by similar means, by introduction of the gene into other organisms and by using similar desaturase genes isolated from yeast or other organisms e.g. field crop plants such as corn, soybeans, rapeseed, etc. to produce a plant which will yield high levels of oils with specific fatty acid compositions.

The following is an hypothesis concerning the overproduction of triglycerides in yeast cells containing multiple copies of fatty acid desaturase encoding genes or enhanced enzyme activity created by the presence of such a gene. It should be noted that the claimed invention should not be limited by this hypothesis which is presented merely as an aid to understanding the underlying mechanism bringing about the observed over-production of oils. It is believed that the over-production of functional fatty acid desaturase enzyme in the cells (believed to be due to the over expression of the gene caused by the presence of multiple copies of the plasmid) leads to the insertion of an increased number of fatty acid desaturase enzyme molecules into the membranes of the cells. The increased number of enzyme molecules in turn leads to production of abnormally high levels of unsaturated fatty acids in the membrane lipids. In order to compensate for the increased levels of unsaturated fatty acids in the lipids, excess unsaturated fatty acids are removed from the membrane lipids and shunted into triglyceride formation. The overproduction of unsaturated fatty acids also has a secondary effect of stimulating the cells to produce more saturated fatty acids in order to compensate for the loss of fatty acids in the membrane lipids and to compensate for the high levels of unsaturated fatty acids. This results in continual over-production of lipids, the net result of which is massive over-production of the triglycerides.

This hypothesis has several implications: (1) introduction of any fatty acid desaturase gene (including several different types of desaturases in the same cell) which are normally not found in the host cells but can be made to function there should result in the over-production of triglycerides; (2) the major fatty acid found in those triglycerides would probably be the product of the last enzyme in the desaturation metabolic pathway, leading to the feasibility of producing oils with highly defined fatty acyl composition; and (3) the regulation of membrane lipid composition by shunting excess membrane fatty acids into triglycerides is probably a general phenomenon. This implies that introduction of excess levels of functional desaturases or other fatty acid modifying enzymes into organisms such as, but not limited to, field crops (soybeans, sunflowers, corn, rapeseed, etc.) would lead to a similar over-production of oils with specialized fatty acid compositions. By constructing plant strains which would produce oils with highly specialized fatty acid compositions it would be possible to produce oils more economically than at present by (1) lowering the costs of refining oils or modifying oils to remove polyunsaturated fatty acids which cause the oil to oxidize easily thus reducing its quality and (2) reducing the costs of blending oils in the correct compositions to produce food and cooking oils which have characteristic melting and boiling temperatures.

The discovery of this process occurred through a series of experiments attempting to examine whether mutated genes which cause an unsaturated fatty acid requirement in yeast were identical to an isolated DNA sequence which encodes the delta-9 fatty acid desaturase enzyme. The isolated (cloned) gene sequence and the unsaturated fatty acid requiring mutant strains were isolated using standard techniques. Plasmids containing the 4.8 kilobase DNA fragment which includes the desaturase gene (as determined by the finding of extensive homology to the rat liver delta-9 desaturase by DNA sequence analysis) were introduced into the mutant cells by spheroplast or lithium transformation procedures. Those plasmids containing the gene sequence also contained portions of the yeast 2 micron circle origin of replication which results in the production of multiple copies of the plasmid in yeast cells.

Cultures of cells containing the plasmid were observed to grow on medium which did not contain unsaturated fatty acids. Microscopic examination of the plasmid containing cell cultures showed that certain proportions of the cells grew as clumps of enlarged cells. Within the enlarged cells were large oil droplets which resembled the triglyceride droplets which are found in adipose tissue. In some cells the droplets occupied greater than 50 percent of the total volume of the cells.

Verification that the oil droplets produced in plasmid bearing strains were triglyceride was done by using the fluorescent stain Nile Red to stain yeast cells in the cultures. Nile Red has a characteristic fluorescence when it is associated with triglyceride droplets. Wild type cells which did not contain the plasmid showed no oil droplets under phase contrast microscopy (Table 3) and showed no fluorescence when stained with Nile Red (Table 3). All mutant cells containing the plasmid showed oil droplets of varying size with phase contrast microscopy (Table 1) and all fluoresced intensely with Nile Red (Table 1) indicating the presence of large amounts of triglycerides. Multiple copies of the plasmid have been introduced into wild-type cells with the effect that many oil droplets are also formed in the cells also causing the cells to fluoresce intensely when stained with Nile Red indicating over-production of triglycerides. Thus the over-production of triglycerides is related to properties associated with multiple copies of the plasmid rather than other properties of the mutant cells.

TABLE 3

| | Presence of Oil Droplets in Transformed Cells | |
|---|---|---|
| Cell Type | Phase Contrast Microscopy | Fluorescence Microscopy* |
| Wild type, no plasmid | 0 | 0 |
| Ole mutant + multiple copy plasmid | + | + |

*based on Nile Red staining procedures detailed herein
+ = presence of droplets or fluorescence Standard molecular genetic methods can be used to isolate the desaturase enzyme, to producing the plasmid vectors and to fuse the plasmid containing the desired gene with appropriate regulatory elements to form a vector which is then introduced into the host cells, e.g., yeast or crop plants. For example, methods for fragmentation of cellular DNA by endonucleases and isolation of the fragments can be found in Maniatis, T., Fritsch, E. F., and Sambrook, J. (1982) *Molecular Cloning: A Laboratory Manual*, Cold Spring Harbor Laboratory, Cold Spring Harbor, N.Y. which is incorporated herein by reference.

Further, a description of the lithium acetate transformation procedure for introducing the vector containing the desired DNA fragment can be found with reference to a publication by H. Ito et. al. "Transformation of Intact Yeast Cells with Alkali Cations" J. Bacteriology 153, 163–168 (1983). Alternatively, one may employ the spheroplast transformation procedure described by F. Sherman et. al. in "Methods in Yeast Genetics", Cold Spring Harbor Laboratories (1984) which also described standard yeast growth medium employed in this work. All of the above publications are incorporated herein by reference. The particular transformation procedure employed is not critical to oil production as evidenced by the fact that both procedures as well as variations thereof give similar results.

It is important for the production of large quantities of oil that the gene causing the oil production be introduced on either a multiple copy plasmid or under the control of an inducible strong promoter (such as, but not limited to the yeast GAL promoters) to allow for over expression of the gene. Yeast cells are grown by standard commercial methods, harvested and oils extracted by standard commercial processes. Alternatively, the yeast cake itself could be sold as a vitamin or health food supplement or as a commercial source of a specialty oil. Genes introduced into plant cells would be under the control of plant developmental genetic regulatory elements with high expression promoters in order to be expressed appropriately in the seeds or alternatively, expression of the genes for oil production could be activated in other plant tissues at a time which would not interfere with optimal plant growth and development.

It is also contemplated that the cloned delta-9 desaturase gene be used to isolate other desaturase genes (e.g. delta-12 and delta-15) from plants and other organisms. Modifications of these genes could be constructed and reintroduction into a plant or other appropriate organism will cause the production of oils with highly specific compositions such as, but not limited to the over-production of linoleic acid and under production of linolenic acid, making a superior product. Using engineered yeast to produce omega-3 fatty acids could provide a more convenient process of isolating the oils in pure form that the current methods of isolation from fish oils. These fatty acids have pharmaceutical value. Engineering yeast or plant strains to produce omega-3 fatty acids would require the introduction of several fatty acid desaturase genes into the organisms such as those that encode the delta-4 and delta-5 enzymes in addition to appropriate elongating enzymes. An alternative approach would be to introduce only the required desaturating enzymes and to feed yeast cultures fatty acids of the appropriate 20–22 carbon chain length.

The construction of a strong expression vector containing the yeast delta-9 fatty acid desaturase gene is shown in FIG. 1. This represents only one example of how such an expression vector can be constructed; other examples may involve the use of:

1. A single copy (centromere containing) vector; or
2. An integrating vector; or
3. A different promoter can be substituted for the GAL-1 promoter; or
4. A different terminator sequence can be used; or
5. A different restriction fragment can be used provided the delta-9 desaturase gene or a similar fatty acid modifying gene is contained therein.

The starting plasmid, YEp352(ole), is an E. coli/yeast shuttle vector used for the expression of genes which contain a promoter which functions in yeast. The plasmid contains the 4.8 kb HindIII restriction fragment, AMP designates the ampicillin resistance gene necessary for selective growth in ampicillin containing media in E. coli and URA-3 designates the gene needed for selective growth in minimal media for yeast cells containing the ura-3 mutation.

EXAMPLE 1

Construction of a *Saccharomyces Cerevisiae* Strain Responsible for Increased Oil Production a. Isolation of a DNA fragment containing the delta-9 desaturase gene from yeast.

A standard haploid genetic strain of *Saccharomyces cerevisiae* containing a mutation in the URA-3 gene so that the strain requires uracil is mated to unsaturated fatty acid requiring strain KD115 (obtained from the Yeast Genetics Stock Center, Berkeley, Calif.) or to mutant strains isolated in this laboratory that require unsaturated fatty acids and are allelic to strain KD115. Diploid cells are sporulated and haploid progeny containing both the unsaturated fatty acid requirement and uracil requirement are isolated using standard genetic methods as described previously. The haploid progeny are then transformed by standard methods using a DNA library constructed by ligating HindIII cut restriction enzyme fragments of yeast genomic DNA into plasmid YEp352 at the unique HindIII restriction site within that plasmid. Cells are plated on medium lacking both uracil and unsaturated fatty acids. Colonies of cells that grow on this medium are then tested to determine that the transformation to a phenotype that is uracil non-requiring (URA+) and unsaturated fatty acid non-requiring (OLE+) is due to the incorporation of a plasmid that contains both the URA-3+ gene and a gene that repairs the fatty acid requirement. That test involves plating individual colonies on non-selective agar medium containing both uracil and unsaturated fatty acids. Under those conditions, a number of the plated cells will lose the transforming plasmid. Cells that contain plasmids with the OLE+ gene will show simultaneous reversion to the ura-, ole-phenotype upon loss of the plasmid.

b. Characterization of OLE+ transforming DNA associated with the plasmid.

Total yeast DNA is isolated from transformed strains that show appropriate co-reversion of both genes on non-selective medium and used to transform strains of *E. coli* for amplification, purification and analysis of the gene sequence inserted on the plasmid using standard methods such as stated in Maniatis, et al. (supera) and Ausubel, F. M. et al., *Current Protocols in Molecular Biology*, (Greene Publishing Associates, Wiley Interscience, Brooklyn, N.Y.) which is herein incorporated by reference. Verification that the cloned DNA fragment contains a structural gene for the delta-9 fatty acid desaturase is obtained using methods such as (1) a determination that the DNA sequence contains an open reading frame with a high degree of sequence similarity and identity to the previously cloned desaturase genes, or (2) a demonstration that the isolated protein synthesized by the cloned gene is capable of restoring fatty acid desaturase activity in vitro to a membrane fraction or a reconstituted system containing all components of the fatty acid desaturating system except for the fatty acid desaturase or (3) a demonstration that the protein encoded by the cloned gene restores fatty acid desaturase activity in vivo when introduced into cells lacking a functional desaturase due to disruption or loss of the normal gene.

c. Introduction of multiple copies of the cloned gene into host *Saccharomyces cerevisiase*.

The plasmid YEp352(ole) is introduced into a ura-3 (uracil requiring) strain of yeast by the previously referred to lithium chloride or spheroplast transformation procedures. URA+ transformants are isolated by growth on medium lacking uracil. Those transformants should have the functional desaturase gene since it resides on the same plasmid as the URA3+ gene. Tests to verify that a functional desaturase gene is in fact introduced into the cells can be performed by RNA hybridization procedures using parts of the original cloned 4.8 kb DNA fragment as probes to measure messenger RNA production associated with the desaturase gene. A culture of the ura-3 mutant transformed with YEp352 (ole) plasmid as described herein was deposited with the American Type Culture Collection, 12301 Parklawn Drive, Rockville, Md. 20852 on Mar. 7, 1991 and after viability was confirmed assigned accession number ATCC 74039. Introduction of the multiple copy plasmid into commercial strains of yeast may be further brought about by methods such as spheroplast fusion procedures in which commercial strains are fused with genetic strains of yeast containing the incorporated plasmid. A review of current genetic yeast engineering methods is contained Developments in Industrial Microbiology, Volume 29 and is incorporated herein by reference.

d. Growth of genetically engineered, oil producing strains.

Strains containing the YEp352(ole) plasmid are grown on carbon sources containing reduced levels of uracil to promote maximal copy number of the plasmid within the cells. This could be standard laboratory media containing amino acid supplements (Sherman, F. supra) or for commercial applications, starch or other carbon sources used in fermentation processes or in baking.

e. Identification and characterization of oil bearing strains of yeast and other organisms.

Engineered strains can be tested for enhanced oil production by fluorescence microscopy using Nile Red as a stain specific for triglycerides. A more quantitative test is to extract total lipids from yeast and to measure levels of triglycerides, diglycerides and fatty acids by standard lipid fractionation procedures. Quantitative tests for triglycerides, diglycerides and fatty acids and fatty acid compositions of the various oils are described in M. Kates, Techniques of Lipidology, in *Laboratory Techniques in Biochemistry and Molecular Biology*, T.S. Work and E. Work, eds., North Holland/American Elsevier Publishing company which is herein incorporated by reference.

f. Extraction and processing of oil.

Yeast cultures grown to optimal density are then harvested using standard commercial procedures and used directly as a food or vitamin source. Alternatively, oils may be extracted from the yeast cake by standard commercial procedures by high pressure extrusion or extraction with solvents such as hexane.

EXAMPLE 2

Use of the Cloned Gene Sequence as a Probe to Isolate other Desaturase Gnees from Yeast or other Organisms; Introduction of those Desaturase Genes into a Yeast or Plant Under Conditions which Lead to High Expression for the Purposes of Modifying the Oil Produced and its Fatty Acid Composition a. Isolation of related desaturase genes from yeast and other organisms.

Regions of the cloned yeast DNA sequence described in Example 1a which have a high similarity (sequence of bases in the DNA or sequences of amino acids in the encoded protein) to other fatty acid desaturase genes are used to isolate desaturase genes encoding enzymes such as the delta-12, delta-15, delta 5 and delta-4 fatty acid desaturases. These isolation procedures may employ selection of related gene sequences from DNA libraries of organisms such as yeast or fungal strains, or field crops such as soybeans, rapeseed, corn, maize, etc. by colony or plaque DNA hybridization methods as generally described in Maniatis (supra) or in Ausubel, F. M. et al., (supra.) Alternatively, fusion proteins constructed from sequences encoding the gene or synthetic peptides constructed from the amino acid sequence of the gene determined from its DNA sequence may be used to prepare antibodies specific for regions of fatty acid desaturase proteins. Those antibodies may then be used to isolate gene sequences encoding related desaturases from libraries constructed in "expression vectors", (bacteriophage, plasmids or other vectors) by methods or methods related to those cited in references incorporated above. A related desaturase, such as a delta-12 desaturase isolated from soybeans may then be reintroduced into that plant or other organisms under the control of strong promoter elements for the purposes of increasing the production of oils containing increased levels of linolenic (9, 12) acid thus changing both the quantities of the oil produced and its fatty acid composition. Either single genes encoding one desaturase (such as the delta-9 desaturase) or multiple genes encoding several desaturases may be incorporated in such a manner for the purposes of producing oils with unique fatty acid compositions. Alternatively, those skilled in the art will also recognize that isolated genes for desaturases may be used to inactivate or otherwise control the expression of one or more desaturase enzymes in a given organism for the purposes of producing oils of a given composition.

An example of this type of control is to use sequences of a delta-12 desaturase that are complementary to the messenger RNA encoding that protein in a plant under the control of promoters which are active during seed development in order to specifically inactivate the synthesis of the delta-12 desaturase protein by "antisense" regulation methods. Methods related to antisense regulation of genes are described in the 1986 American Society for Cell Biology 1986 Education Committee Workshop Manual entitled "*Molecular Genetic Approaches to the Study of Cell Structure and Function*" by R. L. Chisholm and L. A. Leinwand. The inactivation of the delta-12 desaturase in soybeans or other crop plants during development of seeds or other oil-bearing tissues would have the effect of producing an oil which is enriched in stearic and oleic acids which would have commercial value as a substitute for cocoa butter. Inactivation or enhanced expression of other desaturases in field crops would lead to the ability to engineer oils with specific compositions for specific applications in an economically favorable manner.

A general technique which may be employed to isolate a related desaturase producing gene in one organism utilizing a gene or gene sequence of a second organism is as follows. First a gene library is formed e.g., by the introduction into cells of a host organism such as *E. Coli* various gene sequences encoding for desaturase enzymes derived from one or more other organisms such that different *E. Coli* host cells contain different genes or gene segments encoding for different desaturase enzymes introduced thereto. Then a nucleic acid probe for a desaturase enzyme is formed. Such probes can be constructed by known methods, for example from cloned yeast cells; from restriction fragments containing the desired regions of a yeast gene, i.e., containing the desired nucleic acid sequences which will allow for identification of a desaturase gene from the library; and from synthetic nucleic acid sequences. Separate colonies or plaques of cells contained in the gene library are then grown e.g. on a growth media in a a petri dish (master plate) where a replica of the colonies can be transferred to a filter paper. The filter paper is then treated with a solution containing the probe. The probe which may be made to be radioactive or fluorescent for easy identification adheres to complimentary nucleic acid sequences found in various members of the gene library allowing identification of those colonies or cells having related nucleic acid sequences and hence isolation of those cells from the master plate. These cells may then be cloned or otherwise used, such as by isolating the desaturase gene, forming an expression vector containing the gene and introducing it into another organism e.g., a plant cell to alter the quantity or composition of oils produced thereby.

In a similar manner, one can produce antibodies which are specific to fatty acid desaturase enzyme protein by known method. The antibodies can then be employed as a probe by exposing the antibodies to a gene library in an expression vector containing the desired gene encoding for a fatty acid desaturase enzyme. The antibody binds to the enzyme produced by the gene enabling identification and isolation of cells containing desaturase genes from the gene library. Antibodies may be constructed for example from fusion proteins formed from sequences encoded by the gene or from synthetic polypeptides prepared from the amino acid sequence encoded by the gene.

As indicated, one may control gene behavior i.e., controlling the expression of a gene encoding for a desaturase enzyme to produce oils of a desired composition, by means of introducing nucleic acid sequences of a gene encoding a desaturase protein into seeds of a plant, which sequences produce an RNA that is complementary to the messenger RNA encoding that protein in the plant in order to inactivate the synthesis of the enzyme and thus alter the type of oil production of the plant. A method for introducing such sequences into plants known to those skilled in the art involves insertion of a DNA fragment, containing regions of a gene encoding the enzyme, into a vector in the "antisense orientation" with respect to the promoter that is active during seed development that controls the transcription of a messenger RNA from the DNA fragment and then the insertion of that vector into the plant.

TABLE 2

DNA SEQUENCE OF A REGION OF 4.8 KB HINDIII FRAGMENT
CONTAINING THE DELTA-9 DESATURASE GENE
(LISTED FROM THE 5'END OF THE SEQUENCE)

| | | | | | |
|---|---|---|---|---|---|
| 1 | TTGTATTACG | TAGAATAGAA | CATCATAGTA | ATAGATAGTT | GTGGTGATCA |
| 51 | TATTATAAAC | AGCACTAAAA | CATTACAACA | AAGATGCCAA | CTTCTGGAAC |
| 101 | TACTATTGAA | TTGATTGACG | ACCAATXTCC | AAAGGATGAC | TCTGCCAGCA |
| 151 | GTGGCATTGTC | GACGAAGTCG | ACTTAACGGA | AGCTAATATT | TTGGCTACTG |
| 201 | GTTTGAATAA | GAAAGCACCA | AGAATTGTCA | ACGGTTTTGG | TTCTTTAATG |
| 251 | GGCTCCAAGG | AAATGGTTTC | CGTGGAATTC | GACAAGAAGG | GAAACGAAAA |
| 301 | GAAGTCCAAT | TTGGATCGTC | TGCTAGAAAA | GGACAACCAA | GAAAAAGAAG |
| 351 | AAGCTAAAAC | TAAAATTCAC | ATCTCCGAAC | AXCCATGGAC | TTTGAATAAC |
| 401 | TGGCACCAAC | ATTTGAACTG | GTTGAACATG | GTTCTTGTTT | GTGGTATGCC |
| 451 | AATGATTGGT | TGGTACTTCG | CTCTCTCTGG | TAAAGTACCT | TTGCATTTAA |
| 501 | ACGTTTTCCT | TTTCTCCGTT | TTCTACTACG | CTGTCGGTGG | TGTTTCTATT |
| 551 | ACTGCCGGTT | ACCATAGATT | ATGGTCTCAC | AGATCTTACT | CCGCTCACTG |
| 601 | GCCAXTGAGA | TTATTCTACG | CTATCTTCGG | TTGTGCTTCC | GTTGAAGGGT |
| 651 | CCGCTAAATG | GTGGGGCCAC | TCTCAXAGAA | TTCACCATCG | TTACACTGAT |
| 701 | ACCTTGAGAG | ATCCTTATGA | CGCTCGTAGA | GGTCTATGGT | ACTCCCACAT |
| 751 | GGGATGGATG | CTTTTGAAGC | CAAATCCAAA | ATACAAGGCT | AGAGCTGATA |
| 801 | TTACCGATAT | GACTGATGAT | TGGACCATTA | GATTCCAACA | XAXACACTAC |
| 851 | ATCTTGTTGA | TGTTATTAAC | CGCTTTCGTC | ATTCCAACTC | TTATCTGTGG |
| 901 | TTACTTTTTC | AACGACTATA | TGGGTGGTTT | GATCTATGCC | GGTTTTATTC |
| 951 | GTGTCTTTGT | CATTCAACAA | GCTACCTTTT | GCATTAACTC | CATGGCTCAT |
| 1001 | TACATCGGTA | CCCAACCATT | CGATGACAGA | AGAACCCCTC | GTGACAACTG |
| 1051 | GATTACTGCC | ATTGTTACTT | TCGGTGAAGG | TTACCATAAC | TTCCACCACG |
| 1101 | AATTCCCAAC | TGATTACAGA | AACGCTATTA | AGTGGTACCA | ATACGACCCA |
| 1151 | ACTAAGGTTA | TCATCTATTT | GACTTCTTTA | GTTGGTCTAG | CATACGACTT |
| 1201 | GAAGAAATTC | TCTCAAAATG | CTATTGAAGA | AGCCTTGATT | CAACAAGAAC |
| 1251 | AAAAGAAGAT | CAATAAAAAG | AAGGCTAAGA | TTAACTGGGG | TCCAGTTTTG |
| 1301 | ACTGATTTGC | CAATGTGGGA | CAXACAXACC | TTCTTGGCTA | AGTCTAAGGA |
| 1351 | AAACAXGGGT | TTGGTTATCA | TTTCTGGTAT | TGTTCACGAC | GTATCTGGTT |
| 1401 | ATATCTCTGA | ACA | | | |

What is claimed is:

1. An expression vector comprising a yeast gene encoding a delta-9 fatty acid desaturase enzyme which functions in a yeast cell to induce or enhance oil production.

2. The expression vector recited in claim 1 wherein the oil is a triglyceride.

3. The expression vector recited in claim 1 wherein the expression vector comprises a HindIII restriction site.

4. The expression vector recited in claim 1 wherein the gene is isolated from yeast as a HindIII restriction fragment.

5. The expression vector recited in claim 1 wherein said expression vector contains multiple copies of said gene.

6. The expression vector recited in claim 1 wherein said expression vector further comprises a promoter for said gene.

7. The expression vector recited in claim 6 wherein said promoter is a GAL promoter.

8. A genetically engineered yeast organism transformed by the vector of claim 1.

9. The organism recited in claim 8 having multiple copies of the vector.

10. The organism recited in claim 8 wherein said gene is contained in a restriction fragment obtained from yeast cells.

11. The organism recited in claim 10 wherein said restriction fragment is a HindIII fragment.

12. The organism recited in claim 8 comprising a vector comprising an added gene encoding a delta-9 fatty acid desaturase enzyme and a promoter.

13. The organism recited in claim 12 wherein said promoter is a GAL promoter.

14. A purified DNA comprising the sequence as described in Table 2.

15. A yeast organism transformed with a DNA comprising the sequence set forth in Table 2.

16. The organism according to claim 15 which is ATCC 74039.

17. A method for producing oil in yeast comprising culturing a yeast stain tranformed with an expression vector comprising a gene encoding a delta-9 fatty acid desaturase enzyme in a medium under conditions of time and temperature sufficient to result in oil production by said yeast.

18. The method according to claim 17 wherein said yeast is *Saccharomyces cerevisae*.

19. The method according to claim 18 wherein said yeast is ATCC 74039.

20. The method according to claim 17 which includes the further steps of recovering said oil from said yeast culture.

* * * * *